United States Patent
Ayer et al.

(10) Patent No.: US 6,283,953 B1
(45) Date of Patent: Sep. 4, 2001

(54) OSMOTIC DRUG DELIVERY MONITORING SYSTEM AND METHOD

(75) Inventors: Rupal Ayer, Santa Clara, CA (US); James B. Eckenhoff, deceased, late of Los Altos, CA (US), by Bonnie J. Eckenhoff, legal representative; Stephen A. Berry, Saratoga, CA (US); Gregory R. Stewart, Marlborough, MA (US); Scott D. Jordan, San Francisco, CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/217,822

(22) Filed: Dec. 22, 1998

Related U.S. Application Data
(60) Provisional application No. 60/070,178, filed on Dec. 31, 1997.

(51) Int. Cl.[7] .................... A61K 9/22; A61F 2/00
(52) U.S. Cl. .................... 604/892.1; 424/423
(58) Field of Search .................... 604/20, 21, 890.1, 604/891.1, 892.2, 131; 424/422, 423, 424

(56) References Cited

U.S. PATENT DOCUMENTS

| | | |
|---|---|---|
| H150 | 11/1986 | Hankner et al. . |
| 3,732,865 | 5/1973 | Higuchi et al. . |
| 3,845,770 | 11/1974 | Theeuwes . |
| 3,916,889 | 11/1975 | Russell . |
| 3,995,631 | 12/1976 | Higuchi et al. . |
| 3,995,632 | 12/1976 | Nakano et al. . |
| 4,111,202 | 9/1978 | Theeuwes . |
| 4,111,203 | 9/1978 | Theeuwes . |
| 4,140,122 | 2/1979 | Kühl et al. . |
| 4,203,439 | 5/1980 | Theeuwes . |
| 4,243,030 | 1/1981 | Lynch et al. . |
| 4,340,054 | 7/1982 | Michaels . |
| 4,373,527 | 2/1983 | Fischell . |
| 4,439,196 | 3/1984 | Higuchi . |
| 4,457,752 * | 7/1984 | Vadasz .................... 604/135 |
| 4,552,561 | 11/1985 | Eckenhoff et al. . |
| 4,639,244 | 1/1987 | Rizk et al. . |
| 4,865,845 | 9/1989 | Eckenhoff et al. . |
| 4,874,388 | 10/1989 | Wong et al. . |
| 4,923,457 | 5/1990 | Ellingsen . |
| 5,137,727 | 8/1992 | Eckenhoff . |
| 5,223,265 | 6/1993 | Wong . |
| 5,279,608 | 1/1994 | Cherif Cheikh . |
| 5,308,348 | 5/1994 | Balaban et al. . |
| 5,312,389 | 5/1994 | Theeuwes et al. . |
| 5,312,390 | 5/1994 | Wong . |
| 5,421,818 * | 6/1995 | Arenberg .................... 604/21 |
| 5,456,679 | 10/1995 | Balaban et al. . |
| 5,603,953 * | 2/1997 | Herbig et al. .................... 424/473 |
| 5,707,361 * | 1/1998 | Slettenmark .................... 604/131 |
| 5,728,396 | 3/1998 | Peery et al. . |
| 5,925,015 * | 7/1999 | Weyers et al. .................... 604/84 |

FOREIGN PATENT DOCUMENTS 3610825   10/1987   (DE) .

* cited by examiner

Primary Examiner—Sharon Kennedy
(74) Attorney, Agent, or Firm—Cindy A. Lynch; Pauline A. Clarke; D. Byron Miller

(57) ABSTRACT

Performance of delivery systems for delivering beneficial agents to an animal are monitored to determine the delivery rate of the beneficial agent and the proper operation of the beneficial agent delivery device. Performance monitoring can be achieved by monitoring the physical configuration of the implanted osmotic delivery device from the exterior of the body to determine the amount of beneficial agent delivered and/or the delivery rate of the beneficial agent. The monitoring of the physical configuration of the implanted osmotic delivery device may be performed in different manners such as by X-ray or fluoroscopic monitoring of the implant structure or magnetic determination of a piston location within the implant. Performance monitoring can also be achieved by use of a performance marker within the beneficial agent to produce a specifically detectable response which can be measured noninvasively in body fluids or by-products.

19 Claims, 2 Drawing Sheets

OSMOTIC DRUG DELIVERY MONITORING SYSTEM AND METHOD

This application claims the benefit under Title 35, United States Code, §119(e) of U.S. Provisional Application No. 60/070,178 filed on Dec. 31, 1997.

FIELD OF THE INVENTION

The invention relates to an osmotic beneficial agent delivery system. More particularly, the invention relates to a noninvasive monitoring system for monitoring the release of a beneficial agent from an implanted osmotic drug delivery system.

BACKGROUND OF THE INVENTION

Many different types of delivery systems for delivering beneficial agents such as pharmaceuticals for the prevention, treatment, and diagnosis of disease are known in the art. One type of delivery system is the osmotic delivery system in which an osmotic pressure gradient is created to draw an aqueous fluid into a beneficial agent containing member causing the beneficial agent to be delivered. Osmotic delivery systems generally include an implantable member forming a chamber containing the beneficial agent and an osmotic agent which draws an aqueous fluid through the walls of the implantable member causing swelling of the osmotic agent and delivery of the beneficial agent.

Some osmotic delivery systems include a single compartment implantable member and contain both the beneficial agent and the osmotic agent within this single compartment. These devices release the beneficial agent by allowing fluid to be imbibed through the wall of the implantable member into the compartment at a rate determined by the permeability of the wall and the osmotic pressure gradient across the wall. The fluid imbibed into the device mixes with the beneficial agent to form an aqueous solution which is dispensed through an exit passageway of the device. Although these devices are effective for delivery of a beneficial agent which is stable and soluble in aqueous and biological fluids, the devices are ineffective for delivery of many types of beneficial agents which are not soluble or stable in aqueous fluids. Examples of osmotic delivery systems of this type include those described in U.S. Pat. Nos. 3,845,770 and 3,916,899.

Improvements in osmotic delivery systems are described in U.S. Pat. Nos. 4,111,202; 4,111,203; and 4,203,439. In these patents the delivery kinetics of the devices has been improved by allowing delivery of beneficial agents without the requirement for the beneficial agent to be soluble in an aqueous type fluid. These improved implantable osmotic devices include a first beneficial agent compartment separated by a film or piston from a second osmotic compartment. In these devices, the beneficial agent is delivered by imbibing fluid through the wall of the device into the osmotic compartment. As the osmotic compartment fills with fluid, the osmotic agent within the compartment swells and acts as a driving force causing the film or piston to move against the beneficial agent and deliver the beneficial agent through a delivery passageway.

The various osmotic delivery systems are designed to deliver a beneficial agent at a controlled rate which will vary depending on many factors including the osmotic material used, the permeability of the walls, and the physical configuration of the delivery device. Although osmotic delivery devices generally operate very reliably to dispense the desired amount of beneficial agent at the desired rate, it would be beneficial to be able to monitor the delivery of beneficial agent. For example, it would be desirable to be able to detect when the beneficial agent within the delivery device has been completely dispensed and a new device may be needed. It would also be beneficial to detect a malfunction of the device, for example, in some types of osmotic delivery devices employing a piston which separates the osmotic agent and the beneficial agent the piston may become frozen causing the device to malfunction. In addition, monitoring of the delivery rate of the beneficial agent would be desirable to more accurately monitor and control treatment.

Some methods which have been contemplated for monitoring drug delivery from osmotic delivery systems include the measurement of residual amounts of delivered drug in the patient, or radiolabeling the drug composition for detection by X-ray. However, these monitoring methods involve a time delay.

Drug delivery rate s are generally determined f or a particular implantable osmotic device by testing the unimplanted drug delivery device and collecting and measuring the delivered drug in a collection vessel. However, these tests will not account for varying conditions which the drug delivery device will encounter when it is actually implanted within the patient. Therefore, monitoring of the operation of the implanted osmotic drug delivery device would be desirable.

OBJECTS AND SUMMARY OF THE INVENTION

Accordingly, it is an object of the present invention to provide a noninvasive monitoring system for osmotic drug delivery devices which can be used to determine the piston position and/or the drug delivery rate for an implanted osmotic dry delivery device.

In accordance with the present invention, an osmotic delivery device for delivery of a beneficial agent to an animal includes an implantable reservoir having at least one opening for delivery of beneficial agent contained within an interior of the reservoir to an organ of an animal, an osmotic engine causing the release of the beneficial agent contained within the reservoir to the animal, and means for noninvasively measuring the release of the beneficial agent from the reservoir from outside of tissue in which the delivery device is implanted.

In accordance with a more detailed aspect of the invention, the means for noninvasively measuring the release of the beneficial agent from the reservoir includes a first radiopaque marker on a portion of the reservoir and a second radiopaque marker on a movable piston positioned within the reservoir and separating the beneficial agent from the osmotic engine.

In accordance with another more detailed aspect of the invention, the means for noninvasively measuring the release of the beneficial agent from the reservoir includes a magnetic piston positioned within the implantable reservoir between the osmotic engine and the beneficial agent. A gauge is provided for determining the position of the magnetic piston from an exterior of the animal.

In accordance with a further more detailed aspect of the present invention, the means for noninvasively measuring the release of the beneficial agent from the reservoir includes a marker incorporated in the beneficial agent. The marker provides a detectable response which can be measured noninvasively in body fluids or by-products to monitor release of the beneficial agent within the animal.

In accordance with another aspect of the present invention, a method of monitoring performance of an osmotic drug delivery system includes implanting an osmotic drug delivery device having a movable piston in an animal and determining a position of the implanted movable piston within the osmotic drug delivery device from an exterior of the animal.

The present invention provides the advantage of noninvasive, real time monitoring of the performance of an implanted osmotic drug delivery system.

BRIEF DESCRIPTION OF THE DRAWINGS

The invention will be better understood by reference to the drawings in which like reference numbers identify like parts and wherein.

DETAILED DESCRIPTION OF THE PREFERRED EMBODIMENTS

The present invention relates to performance monitoring of implantable osmotic delivery systems for delivery of beneficial agents to animals and/or humans. Performance monitoring according to the present invention can be achieved by either 1) monitoring the physical configuration of the implanted osmotic delivery device from the exterior of the body to determine the amount of beneficial agent delivered and/or the delivery rate of the beneficial agent; or 2) by use of a performance marker within the beneficial agent to produce a specifically detectable response which can be measured noninvasively in body fluids or by-products.

Figure 1:
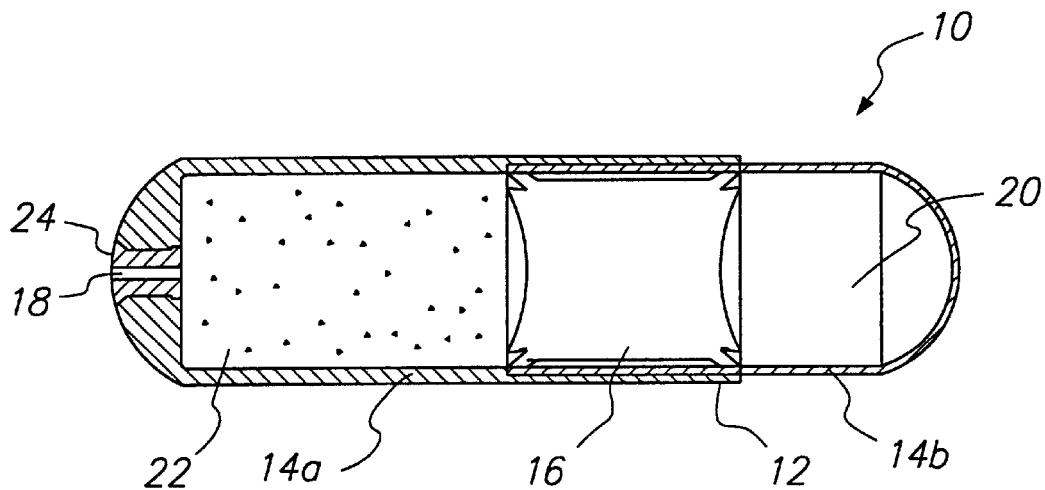
FIG. 1 is a side cross sectional view of an osmotic drug delivery device according to a first embodiment of the invention.

Turning now to FIG. 1, an implantable osmotic delivery system 10 includes an elongated, generally cylindrical housing 12 formed of a first wall 14a and a second wall 14b, an internal movable piston 16, and an exit passage 18 for beneficial agent delivery from the delivery device to the patient. The first and second walls 14a, 14b of the delivery system 10 interengage to define an internal compartment which is divided by the piston 16 into an osmotic chamber 20 and a beneficial agent chamber 22. The second wall 14b of the delivery system includes at least a portion of the wall which is permeable to the passage of aqueous fluid through the wall into the osmotic chamber 20 while the entire wall 14b is impermeable to the osmotic material contained within the osmotic chamber. The fluid permeable portion of the second wall 14b allows fluid to pass into the osmotic agent contained within the chamber 20 and expand the osmotic agent or driving means. The expansion of this osmotic agent, also called an osmotic engine, causes the movable piston 16 to slide within the housing dispensing the beneficial agent from the beneficial agent chamber 22 through the exit passage 18. The first wall 14a is preferably impermeable to both external and internal fluids.

The first and second walls 14a, 14b of the housing provide an easy method of manufacturing the delivery system 10 by inserting or telescoping the second wall 14b into the first wall 14a to form a liquid and gas impermeable seal between the first and second walls. Although the two part housing is used for purposes of ease of manufacturing, a one part housing or other housing configurations may also be used. In addition, other housing shapes may also be used within the scope of the present invention with the diameter of the delivery system 10 varying depending on the desired delivery rates.

The piston 16 according to the first embodiment of the invention illustrated in FIG. 1, is formed of a material which is impermeable to the agents in the two chambers 20, 22. The piston 16 includes a radiopaque dye formulated into the material of the piston such that the piston is visible in an X-ray. In addition, a snap-in flow modulator 24 is provided at an end of the first wall 14a and includes the exit passage 18. The flow modulator 24 is also formulated with a radiopaque dye incorporated into the material of the snap-in member. Examples of acceptable radiopaque dyes include salts of heavy metals, such as bismuth and titanium, barium salts, and other contrast agents, such as the type used for visualization of small catheters.

Using standard X-ray techniques, the design of the implant of FIG. 1 with the radiopaque piston 16 and flow modulator 24 allows the precise location of the piston to be determined with respect to a fixed reference point provided by the flow modulator.

The movement of the piston 16 within the housing 12 of the osmotic delivery device of FIG. 1 can be observed noninvasively by performing successive X-rays over time. The information about the position of the piston 16 in real time and the diameter of the osmotic delivery device are used to determine the in vivo release rate for a known diameter drug delivery system 10. The release rate can be determined by either a comparison of two successive X-rays or by comparison of a single X-ray to a known initial state of the osmotic delivery device.

Figure 2:
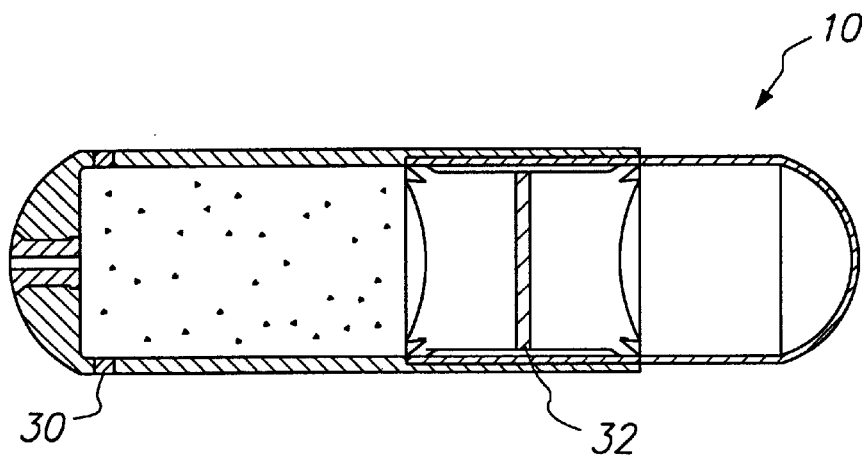
FIG. 2 is a side cross sectional view of an osmotic drug delivery device according to a second embodiment of the invention.

FIG. 2 illustrates an alternative embodiment of the invention in which a first radiopaque ring 30 is provided on the dispensing end of the housing wall 14a and a second radiopaque ring 32 is provided on the piston 16. The relative positions of the two radiopaque rings 30, 32 are measured in real time in a series of X-rays or fluoroscope pictures to determine the beneficial agent delivery rate from the delivery system. The second radiopaque ring 32 may be positioned at any location along the piston 16 and may be formed in any shape. Likewise, the first radiopaque ring 30 may be positioned at any location along the housing 12, as it is the relative locations of these two radiopaque markers 30, 32 which is measured over time.

In addition to the use of X-rays, fluoroscopy can also be used to determine the piston position. In order for the piston location to be determined clearly from a fluoroscope picture, the walls 14a, 14b of the delivery system should be formed of titanium with a purity of at least about 85%. In this instance, no radiopaque markers are needed to determine piston position by fluoroscopy because the purity of the titanium allows fluoroscopy viewing of the piston position within the walls of the implant.

Figure 3:
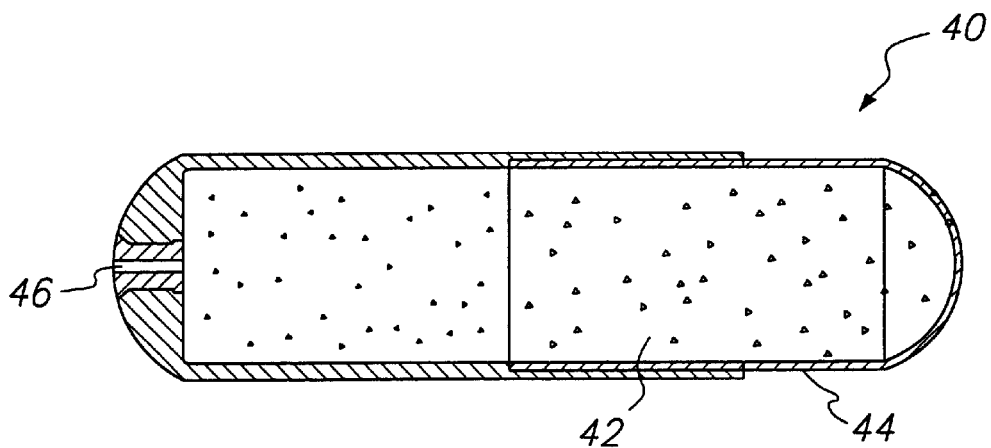
FIG. 3 is a side cross sectional view of an osmotic drug delivery device according to a third embodiment of the invention.

FIG. 3 illustrates another alternative embodiment of the invention in which one or more chemical markers designed to produce a specifically detectable response are incorporated into the beneficial agent to be delivered from an osmotic delivery system. The drug delivery system 40 shown in FIG. 3 includes housing having a single interior chamber 42 containing a beneficial agent which is osmotically active or includes an osmotic agent incorporated into the beneficial agent. The drug delivery system housing includes at least one fluid permeable wall 44 which allows fluid to pass into the chamber 42 but does not allow the beneficial agent and osmotic agent to pass out through the wall. The system 40 also includes a drug delivery or exit passage 46 through which the beneficial agent is delivered to the patient.

The chemical markers which can be incorporated within the beneficial agent in the chamber 42 of an osmotic delivery system such as that shown in FIG. 3 include but are not limited to 1) markers that can be detected noninvasively in body tissues or patient fluid samples; 2) peptides and/or proteins that give specific reagent responses; 3) volatile compounds that are vaporized and detected in expelled breath; and 4) metabolites of the drug being delivered that produce measurable responses. Each of these types of markers allows noninvasive monitoring of the drug delivery by the implanted osmotic delivery device 40. The different types of chemical markers may be used either alone or in combination.

The chemical markers according to the present invention can be used in a wide variety of osmotic delivery systems including a system 40 in which the osmotic agent is incorporated in the beneficial agent, as illustrated in FIG. 3, as well as in a delivery system 10 such as is shown in FIGS. 1 and 2 in which the osmotic agent and beneficial agent are maintained in separable compartments by a piston 16 or flexible membrane. The chemical markers may also be used in combination with each other or with other monitoring systems such as the X-ray monitory system described above.

Markers that can be detected non-invasively in body tissues or patient fluid samples include azo dyes that can be detected either visually or by diagnostic reaction from patient fluid samples. One such dye is a fluorescent dye, such as fluorescein tagged dextrans, which can be tracked through the body under an external fluorescent light source and/or detected in urine by fluorescent light. Other markers may also be released to the circulatory system and can be measured in skin, tongue, eyes, or other tissues by the use of an external light source. Markers which are detectable in a patient's breath include DMSO (dimethylsulfoxide) which emits an odor detectable with a sulfur detector.

Figure 4:
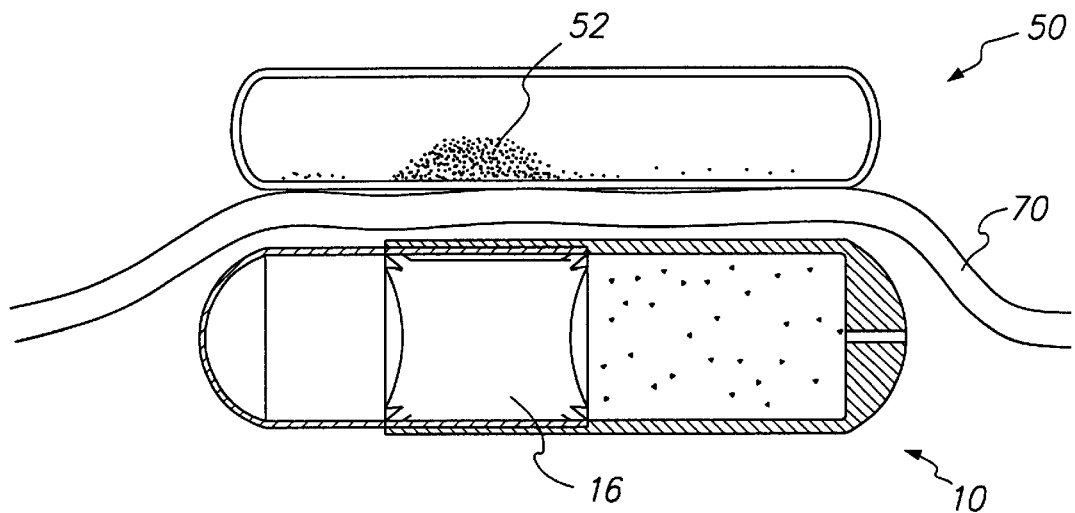
FIG. 4 is a side cross sectional view of an osmotic drug delivery device and gauge according to a fourth embodiment of the invention.

FIG. 4 illustrates a further embodiment of the present invention in which an external gauge 50 is used to determine the location of the piston 16 within an osmotic delivery system 10 of the type described above with respect to the embodiment of FIG. 1. For a complete description of the delivery system 10 used in the embodiment of FIG. 4 reference should be made to the description of FIG. 1 above. The delivery system 10 for use with this embodiment incorporates a magnetic piston 16 which identifies the location of the piston to the external gauge 50. The piston 16 may have magnetic particles imbedded within the piston material, magnetic particles imbedded or sprayed on in a coating of the piston, or the piston may be entirely magnetic.

The gauge 50 is a transparent tube-like device containing magnetic particles 52. The gauge 50 has a length which is substantially the same as the length of the implanted delivery system 10. The location of the implanted device 10 can be seen and felt somewhat through the skin of the animal or human in which it is implanted. Thus, when the implanted system 10 is positioned under a layer of skin 70 of the patient, the gauge 50 can be aligned with the implanted system and the magnetic particles 52 within the gauge will be attracted to and congregate at the location of the piston 16 within the delivery device 10 as shown in FIG. 4. Accordingly, a periodic recording of the location of the congregation of the magnetic particles 52 within the gauge 50 provides feedback on system performance so that the amount of beneficial agent that has been released and/or the delivery rate can be determined. Barring significant failures of the piston, piston movement is in direct correlation to beneficial agent delivery rate.

Figure 5:
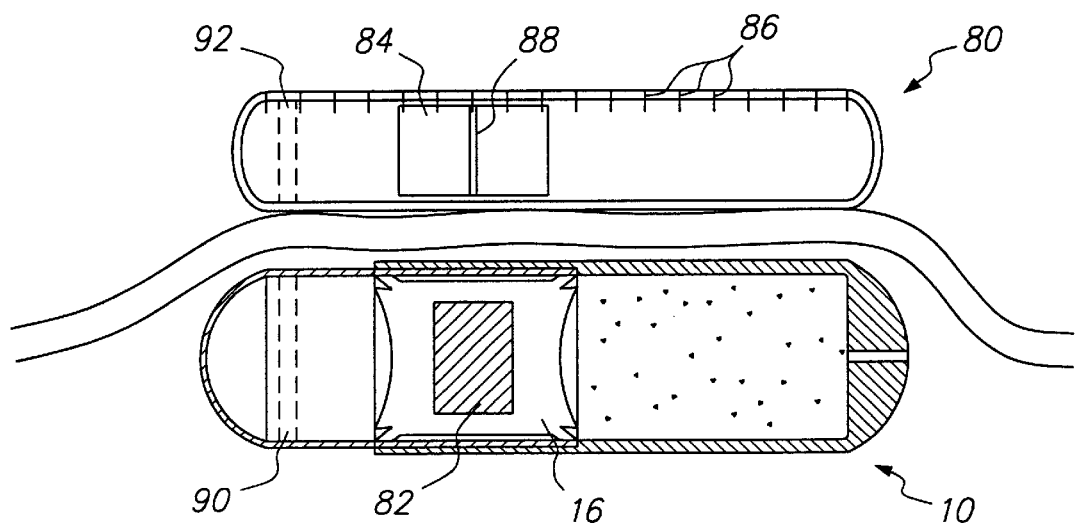
FIG. 5 is a side cross sectional view of an osmotic drug delivery device and gauge according to a fifth embodiment of the invention.

An alternative embodiment of a gauge 80 for determining the location of a piston 16 within an osmotic delivery device 10 is illustrated in FIG. 5. According to this embodiment, the piston 16 is provided with an internal magnet 82 imbedded in the piston. Alternatively, the magnetic material may also be incorporated into the piston in other ways, as discussed above with respect to the embodiment of FIG. 4.

The gauge 80 is a transparent tube having a cylindrical sliding magnet 84 positioned inside the tube. The tube 80 includes markings 86 and the magnet 84 includes an indicator line 88 to facilitate reading of the gauge measurement. The gauge 80 is used in a manner similar to the gauge 50 by periodically placing the clear tube against the implanted delivery device 10 with the ends of the gauge and the delivery device aligned and reading the location of the piston 16 from the markings 86 on the gauge.

The accuracy of the monitoring systems of FIGS. 4 and 5 will depend in large part on the accuracy with which the gauges 50, 80 are aligned with the implanted devices 10. Therefore, it would be beneficial to provide protrusions or other types of guides on the implanted device 10 which can be felt through the skin and will help the user to achieve an accurate alignment between the gauges 50, 80 and the implanted device.

Once the implant 10 has been implanted, it may be difficult to determine the orientation of the implant. Therefore, the implant may be provided with a magnetic band 90 or other indicator at one end corresponding to a magnetic band 92 on the gauge 80. The magnetic bands 90, 92 allow the user to achieve an accurate alignment of the gauge 80 with the implant 10 and prevent unintended inversion of the gauge.

It should be understood that the transparent tubes forming the gauges 50, 80 may also be partially opaque with an elongated transparent window for viewing the magnet or magnetic particles. The gauges 50, 80 may also be entirely opaque and have an external indicator or pointer. Further, the gauge 50 employing magnetic particles can also be used with the osmotic delivery system employing the magnet 82 in the piston 16, and alternatively, the gauge 80 may be used with an osmotic delivery device having a piston 16 with magnetic particles incorporated in the lubrication.

The performance monitoring system according to the present invention provides more up to date and accurate monitoring over the present practice of measuring residual amounts of beneficial agent in the patient to determine the delivery rate.

The expandable driving member or osmotic engine for use in the preferred embodiments of the present invention may be any of the osmotically effective compounds including inorganic and organic compounds that exhibit an osmotic pressure gradient across a semipermeable wall. These osmotically effective compounds as well as manufacturing techniques and materials for formation of the osmotic delivery device itself are described in U.S. Pat. No. 5,057,318, which is incorporated herein by reference.

The beneficial agents delivered according to the present invention include proteins and proteinaceous compounds having biological activity which may be used to treat disease or other pathological condition. These include, but are not limited to growth hormone, Factor VIII, Factor IX and other coagulation factors, chymotrypsin, trypsinogen, alpha-interferon, beta-galactosidase, lactate dehydrogenase, growth factors, clotting factors, enzymes, immune response stimulators, cytokines, lymphokines, interferons, immunoglobulins, interleukins, peptides, somatostatin, somatotropin analogues, somatomedin-C, Gonadotropic releasing hormone, follicle stimulating hormone, luteinizing hormone, LHRH, LHRH analogues such as leuprolide, nafarelin and goserelin, LHRH agonists and antagonists, growth hormone releasing factor, calcitonin, colchicine, gonadotropins such as chorionic gonadotropin, oxytocin, octreotide, somatotropin plus an amino acid, vasopressin, adrenocorticotrophic hormone, epidermal growth factor, prolactin, somatotropin plus a protein, cosyntropin, lypressin, polypeptides such as thyrotropin releasing hormone, thyroid stimulation hormone, secretin, pancreozymin, enkephalin, glucagon, endocrine agents secreted internally and distributed by way of the bloodstream, and the like. Further agents that may be delivered include $\alpha_1$ antitrypsin, insulin and other peptide hormones, adrenal cortical stimulating hormone, thyroid stimulating hormone, and other pituitary hormones, interferon $\alpha$, $\beta$, and $\gamma$, consensus interferon, erythropoietin, growth factors such as GCSF, GM-CSF, insulin-like growth factor 1, tissue plasminogen activator, CF4, DDAVP, tumor necrosis factor receptor, pancreatic enzymes, lactase, interleukin-1 receptor antagonist, interleukin-2, tumor suppressor proteins, cytotoxic proteins, retroviruses and other viruses, viral proteins, antibodies, recombinant antibodies, antibody fragments and the like.

While the preferred embodiments of the present invention have been described, those skilled in the art will appreciate that various modifications, changes, additions, and omissions in the devices illustrated and described can be made without departing from the invention.

What is claimed is:

1. An osmotic delivery device for delivery of a beneficial agent to an animal comprising:
   an implantable reservoir having at least one opening for delivering a beneficial agent contained within an interior of the reservoir to an organ of an animal;
   an osmotic engine adapted to cause the release of the beneficial agent contained within the reservoir to the animal; and
   means for noninvasively measuring the release of the beneficial agent from the reservoir from outside of tissue in which the delivery device is implanted.

2. The osmotic delivery device of claim 1, wherein the means for noninvasively measuring the release of the beneficial agent from the reservoir includes a first radiopaque marker on a portion of the reservoir and a second radiopaque marker on a movable piston positioned within the reservoir and separating the beneficial agent from the osmotic engine.

3. The osmotic delivery device of claim 2, wherein the implantable reservoir includes at least one passage allowing liquid to pass into the osmotic engine to cause the osmotic engine to swell and move the movable piston within the reservoir.

4. The osmotic delivery device of claim 1, wherein the means for noninvasively measuring the release of the beneficial agent from the reservoir includes a magnetic piston positioned within the implantable reservoir between the osmotic engine and the beneficial agent and a gauge for determining the position of the magnetic piston from an exterior of the animal.

5. The osmotic delivery device of claim 4, wherein the gauge for determining the position of the magnetic piston includes a movable magnetic member.

6. The osmotic delivery device of claim 5, wherein the implantable reservoir includes means for aligning the gauge with the reservoir.

7. The osmotic de livery device of claim 4, wherein the magnetic piston includes magnetic particles in a piston lubricant.

8. The osmotic delivery device of claim 1, wherein the means for noninvasively measuring the release of the beneficial agent from the reservoir includes a marker incorporated in the beneficial agent, the marker providing a detectable response which can be measured noninvasively in body fluids or by-products to monitor release of the beneficial agent.

9. The osmotic delivery device of claim 8, wherein the marker is an azo dye which can be detected in patient fluid samples.

10. The osmotic delivery device of claim 9, wherein the azo dye is visually detected in the fluid samples.

11. The osmotic delivery device of claim 9, wherein the azo dye is detectable in the fluid samples by diagnostic reaction.

12. The osmotic delivery device of claim 8, wherein the marker is a peptide or protein which gives specific reagent responses.

13. The osmotic delivery device of claim 8, wherein the marker is a compound which is vaporized and detectable in expelled breath.

14. The osmotic delivery device of claim 8, wherein the marker is a metabolite of the beneficial agent, the metabolite producing measurable responses.

15. The osmotic delivery device of claim 8, wherein the marker is measurable in tissue by the use of an external light source.

16. A method of monitoring performance of an osmotic drug delivery system comprising:
   implanting an osmotic drug delivery device having a movable piston in an animal; and
   determining a position of the implanted movable piston within the osmotic drug delivery device from an exterior of the animal.

17. The method of monitoring performance of the osmotic drug delivery system according to claim 16, wherein the position of the movable piston is determined by fluoroscopy.

18. The method of monitoring performance of the osmotic drug delivery system according to claim 16, wherein the position of the movable piston is determined by X-ray.

19. The method of monitoring performance of the osmotic drug delivery system according to claim 16, wherein the position of the movable piston is determined by a magnetic gauge.

* * * * *